United States Patent [19]
Gregg et al.

[11] Patent Number: 5,883,109
[45] Date of Patent: Mar. 16, 1999

[54] METHOD FOR LOWERING SERUM LIPID LEVELS EMPLOYING AN MTP INHIBITOR IN COMBINATION WITH ANOTHER CHOLESTEROL LOWERING DRUG

[75] Inventors: Richard E. Gregg, Pennington; Hubert G. Pouleur, Lawrenceville, both of N.J.; John R. Wetterau, II, Langhorne, Pa.

[73] Assignee: Bristol-Myers Squibb Company, Princeton, N.J.

[21] Appl. No.: 854,311

[22] Filed: May 12, 1997

Related U.S. Application Data

[60] Provisional application No. 60/022,866 Jul. 24, 1996.
[51] Int. Cl.[6] ............................................. A61K 31/445
[52] U.S. Cl. ........................... 514/321; 514/325; 514/824
[58] Field of Search ................................... 514/321, 325, 514/824

[56] References Cited

U.S. PATENT DOCUMENTS

| | | | |
|---|---|---|---|
| 3,674,836 | 7/1972 | Creger | 260/473 G |
| 3,910,931 | 10/1975 | Cavalla et al. | 260/293.62 |
| 4,289,781 | 9/1981 | Bengtsson et al. | 424/267 |
| 4,346,277 | 8/1982 | Wojtecki et al. | 219/528 |
| 4,367,232 | 1/1983 | Boix-Igleasias et al. | 424/267 |
| 4,576,940 | 3/1986 | Tahara et al. | 514/212 |
| 4,581,355 | 4/1986 | Tahara et al. | 514/212 |
| 4,607,042 | 8/1986 | Pierce | 514/323 |
| 4,826,975 | 5/1989 | Picciola et al. | 544/391 |
| 5,026,858 | 6/1991 | Vega-Noverola et al. | 546/224 |
| 5,028,616 | 7/1991 | Desai et al. | 514/321 |
| 5,032,598 | 7/1991 | Baldwin et al. | 514/318 |
| 5,098,915 | 3/1992 | Desai et al. | 514/324 |
| 5,130,333 | 7/1992 | Pan et al. | 514/460 |
| 5,189,045 | 2/1993 | Peglion et al. | 514/319 |
| 5,212,182 | 5/1993 | Musser et al. | 514/314 |
| 5,215,989 | 6/1993 | Baldwin et al. | 514/252 |
| 5,292,883 | 3/1994 | Martin et al. | 546/201 |
| 5,470,845 | 11/1995 | Magnin et al. | 514/121 |
| 5,527,801 | 6/1996 | Masuda et al. | 514/255 |

FOREIGN PATENT DOCUMENTS

| | | |
|---|---|---|
| 0584446A2 | 3/1994 | European Pat. Off. |
| 0643057A1 | 3/1995 | European Pat. Off. |
| WO93/05778 | 9/1991 | WIPO |
| WO96/40640 | 12/1996 | WIPO |
| WO97/26240 | 7/1997 | WIPO |

OTHER PUBLICATIONS

Bulleid & Freedman, Nature 335, 649–651 (1988). "Defective co–translational formation of disulphide bonds in pro-tein disulphideisomerase–deficient microsomes".

Koivu et al., J. Biol. Chem. 262, 6447–6449 (1987). "A Single Polypeptide Acts Both as the β Subunit of Prolyl 4–Hydroxylase and as a Protein Disulfide–Isomerase*".

Kane & Havel in the Metabolic Basis of Inherited Disease, Sixth Edition, 1139–1164 (1989). "Disorders of the Biogenesis and Secretion of Lipoproteins Containing The B Apolipoproteins".

Schaefer et al., Clin. Chem. 34, B9–B12 (1988). "Genetics and Abnormalities in Metabolism of Lipoproteins".

Drayna et al., Nature 327, 632–634 (1987). "Cloning and sequencing of human cholesteryl ester transfer protein cDNA".

Pihlajaniemi et al., EMBO J. 6, 643–649 (1987). "Molecular cloning of the β–subunit of human prolyl 4–hydroxylase. This subunit and protein disulphide isomerase are products of the same gene".

Yamaguchi et al., Biochem. Biophys. Res. Comm. 146, 1485–1492 (1987). "Sequence of Membrane–Associated Thyroid Hormone Binding Protein From Bovine Liver: Its Identity with Protein Disulphide Isomerase".

Edman et al., Nature 317, 267–270 (1985). Sequence of protein disulphide isomerase and implications of its relationship to thioredoxin.

Kao et al., Connective Tissue Research 18, 157–174 (1988). "Isolation of cDNA Clones and Genomic DNA Clones of β–Subunit of Chicken Prolyl 4–Hydroxylase*".

Wetterau, J. et al., Biochem 30, 9728–9735 (1991). "Protein Disulfide Isomerase Appears Necessary To Maintain the Catalytically Active Structure of the Microsomal Triglyceride Transfer Protein".

Morton, R.E. et al., J. Biol. Chem. 256, 1992–1995 (1981). "A Plasma Inhibitor of Triglyceride and Chloesteryl Ester Transfer Activities".

Wetterau, J. et al., Biochem. 30, 4406–4412 (1991): "Structural Properties of the Microsomal Triglyceride–Transfer Protein Complex".

Wetterau, J. et al., J. Biol. Chem. 265, 9800–9807 (1990). "Protein Disulfide Isomerase Is a Component of the Microsomal Triglyceride Transfer Protein Complex".

Wetterau, J. and Zilversmit, D.B., Chem. and Phys. of Lipids 38, 205–22 (1985). "Purification and Characterization of Microsomal Triglyceride and Cholesteryl Ester Transfer Protein From Bovine Liver Microsomes".

Wetterau, J. and Zilversmit, D.B., Biochimica et Biophysica Acta 875, 610–617 (1986). "Localization of intracellular triacylglycerol and cholesteryl ester transfer activity in rat tissues".

Wetterau, J. and Zilversmit, D.B., J. Biol. Chem. 259, 10863–10866 (1984), "A Triglyceride and Cholestryl Ester Transfer Protein Associated with Liver Microsomes".

Wetterau, J., Grant Application entitled: "Intracellular Triglyceride Transport and Metabolism". (1987).

(List continued on next page.)

*Primary Examiner*—Kimberly Jordan
*Attorney, Agent, or Firm*—Burton Rodney

[57] ABSTRACT

A method is provided for lowering serum lipids, cholesterol and/or triglycerides and thereby inhibiting atherosclerosis by administering to a patient an MTP inhibitor, in combination with a cholesterol lowering drug, such as pravastatin.

22 Claims, No Drawings

OTHER PUBLICATIONS

Presentation Materials, Aspen Bile Acid/Cholesterol Conference, Aug. 15, 1992.

Wetterau, J. R., et al., Science, vol. 258, 999–1001, Nov. 6, 1992, "Absence of Microsomal Triglyceride Transfer Protein in Individuals with Abetalipoproteinemia".

Archibald, J. L., et al., Journal of Medicinal Chemistry, vol. 14, No. 11, pp. 1054–1059 (1971).

Cortizo, L. et al., J. Med. Chem., 34, pp. 2242–2247, 1991.

Hall, I. H. et al., Pharmaceutical Research, vol. 9, No. 10, pp. 1324–1329, 1992.

Hall, I. H., et al., Pharmacological Research Communications, vol. 19, No. 12, pp. 839–858, 1987.

Murthy et al., Eur. J. Med. Chem.—Chim. Ther., vol. 20, No. 6, pp. 547–550, 1985.

Conn's Current Therapy, W.B. Saunders Company, pp. 504–509, 1992.

METHOD FOR LOWERING SERUM LIPID LEVELS EMPLOYING AN MTP INHIBITOR IN COMBINATION WITH ANOTHER CHOLESTEROL LOWERING DRUG

This application claims the benefit of U.S. Provisional Application No. 60/022,866, filed Jul. 24, 1996.

FIELD OF THE INVENTION

The present invention relates to a method for lowering serum lipids, cholesterol and/or triglycerides in mammalian species by administering an MTP inhibitor in combination with another cholesterol lowering drug, for example, an HMG CoA reductase inhibitor, such as pravastatin, lovastatin or simvastatin.

BACKGROUND OF THE INVENTION

The use of microsomal triglyceride transfer protein (MTP) inhibitors for decreasing serum lipids including cholesterol and triglycerides and their use in treating atherosclerosis, obesity and pancreatitis is disclosed in Canadian Patent Application No. 2,091,102 (corresponding to U.S. application Ser. No. 117,362, now U.S. Pat. No. 5,595,872), U.S. application Ser. No. 472,067, filed Jun. 6, 1995, now U.S. Pat. No. 5,739,135 (file DC21e), U.S. application Ser. No. 548,811, now U.S. Pat. No. 5,712,279 (file DC21h), U.S. provisional application No. 60/017,224, (file HX79a*), U.S. provisional application No. 60/017,253, (file HX82*) and U.S. provisional application No. 60/017,254, (file HX84*).

All of the above U.S. applications are incorporated herein by reference.

DESCRIPTION OF THE INVENTION

In accordance with the present invention, a method for preventing, inhibiting or treating atherosclerosis, pancreatitis or obesity is provided, wherein an MTP inhibitor in combination with another cholesterol lowering drug is administered in therapeutically effective amounts to lower LDL cholesterol and triglycerides.

Furthermore, in accordance with the present invention, a method is provided for lowering serum lipid levels, cholesterol and/or triglycerides, or inhibiting and/or treating hyperlipemia, hyperlipidemia, hyperlipoproteinemia, hypercholesterolemia and/or hypertriglyceridemia, wherein a combination of an MTP inhibitor and another cholesterol lowering drug is administered in therapeutically effective amounts.

In addition, in accordance with the present invention, a novel combination of cholesterol lowering agents is provided which includes an MTP inhibitor and another cholesterol lowering drug.

Cholesterol lowering drugs or drugs which are inhibitors of cholesterol biosynthesis which may be used in the method of the invention in combination with the MTP inhibitor include HMG CoA reductase inhibitors, squalene synthetase inhibitors, fibric acid derivatives, bile acid sequestrants, probucol, niacin, niacin derivatives, neomycin, aspirin, and the like.

It is believed that the combination of MTP inhibitor and other cholesterol lowering drug, which works by a mechanism other than inhibiting MTP, is a surprising and unique concept in treating diseases involved with elevated cholesterol and/or triglycerides and atherosclerosis, obesity and/or pancreatitis, in that the combination may provide additional anticholesterolemic effects over that which may be obtained using each of the components of the combination alone. It is expected that reduced levels of each of the MTP inhibitor and other cholesterol lowering drug may be employed to achieve desired results, albeit with reduced side effects.

DETAILED DESCRIPTION OF THE INVENTION

The following definitions apply to the terms as used throughout this specification, unless otherwise limited in specific instances.

The term "MTP" refers to a polypeptide or protein complex that (1) if obtained from an organism (e. g., cows, humans, etc.), can be isolated from the microsomal fraction of homogenized tissue; and (2) stimulates the transport of triglycerides, cholesterol esters, or phospholipids from synthetic phospholipid vesicles, membranes or lipoproteins to synthetic vesicles, membranes, or lipoproteins and which is distinct from the cholesterol ester transfer protein [Drayna et al., Nature 327, 632–634 (1987)] which may have similar catalytic properties.

The phrase "stabilizing" atherosclerosis as used in the present application refers to slowing down the development of and/or inhibiting the formation of new atherosclerotic lesions.

The phrase "causing the regression of" atherosclerosis as used in the present application refers to reducing and/or eliminating atherosclerotic lesions.

The combination of the MTP inhibitor and other cholesterol lowering drug will be employed in a weight ratio to each other of within the range of from about 1000:1 to about 0.001:1 and preferably from about 0.05:1 to about 100:1.

MTP inhibitors to be employed in the methods of the invention include MTP inhibitors disclosed in Canadian Patent Application No. 2,091,102 (corresponding to U.S. application Ser. No. 117,362, now U.S. Pat. No. 5,595,872), U.S. application Ser. No. 472,067, filed Jun. 6, 1995, now U.S. Pat. No. 5,739,135 (file DC21e), U.S. application Ser. No. 548,811, now U.S. Pat. No. 5,712,279 (file DC21h), U.S. provisional application No. 60/017,224, (file HX79a*), U.S. provisional application No. 60/017,253, (file HX82*) and U.S. provisional application No. 60/017,254, (file HX84*).

All of the above U.S. applications are incorporated herein by reference.

The MTP inhibitors disclosed in U.S. application Ser. No. 472,067, filed Jun. 6, 1995, now U.S. Pat. No. 5,739,135 (file DC21e) are piperidine compounds of the structure

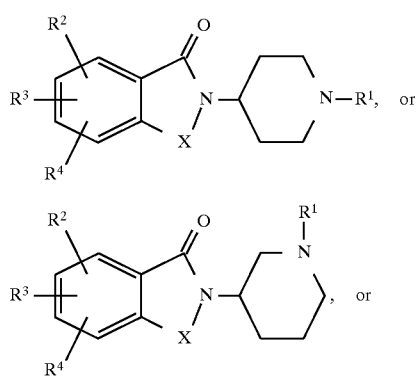

-continued

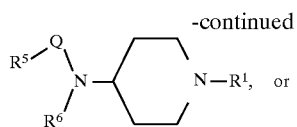

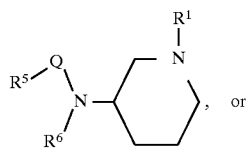

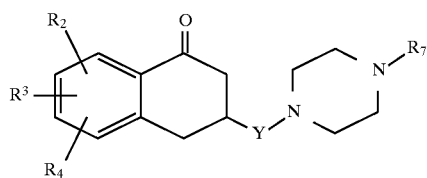

where Q is

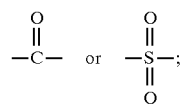

X is: CHR$^8$,

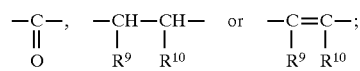

R$^8$, R$^9$ and R$^{10}$ are independently hydrogen, alkyl, alkenyl, alkynyl, aryl, arylalkyl, heteroaryl, heteroarylalkyl, cycloalkyl, or cycloalkylalkyl;

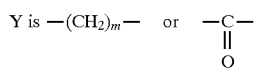

wherein m is 2 or 3;

R$^1$ is alkyl, alkenyl, alkynyl, aryl, heteroaryl, arylalkyl wherein alkyl has at least 2 carbons, diarylalkyl, arylalkenyl, diarylalkenyl, arylalkynyl, diarylalkynyl, diarylalkylaryl, heteroarylalkyl wherein alkyl has at least 2 carbons, cycloalkyl, or cycloalkylalkyl wherein alkyl has at least 2 carbons, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cyclo-alkylalkyl, heteroaryl, fluorenyl, heteroarylalkyl, hydroxy or oxo;

or R$^1$ is a fluorenyl-type group of the structure

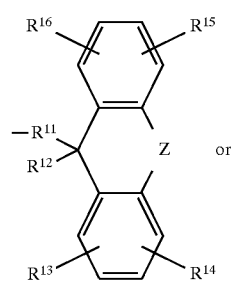
A

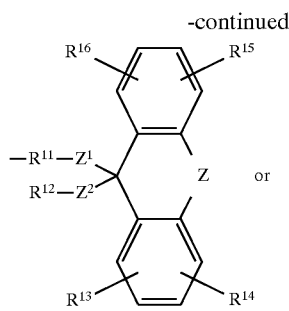
B

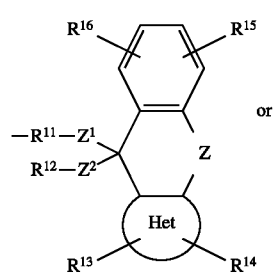
C

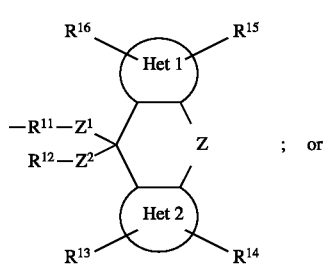
D

R$^1$ is an indenyl-type group of the structure

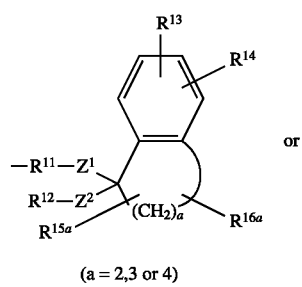
E (a = 2, 3 or 4)

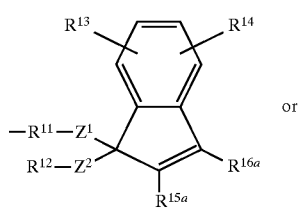
F

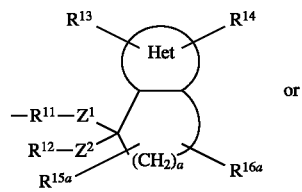
G

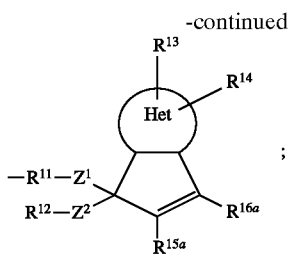

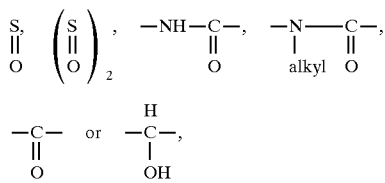

$Z^1$ and $Z^2$ are the same or different and are independently a bond, O, S,

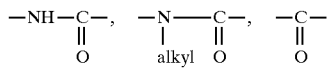

with the proviso that with respect to B, at least one of $Z^1$ and $Z^2$ will be other than a bond; $R^{11}$ is a bond, alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cyclo-alkyl, aryloxy, alkoxy, arylalkoxy or cycloalkyl-alkyl, with the provisos that (1) when $R^{12}$ is H, aryloxy, alkoxy or arylalkoxy, then $Z^2$ is $$-NH-\underset{O}{\overset{C}{\|}}-, \quad -\underset{alkyl}{\overset{N}{|}}-\underset{O}{\overset{C}{\|}}-, \quad -\underset{O}{\overset{C}{\|}}-$$

or a bond and (2) when $Z^2$ is a bond, $R^{12}$ cannot be heteroaryl or heteroarylalkyl;

Z is bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

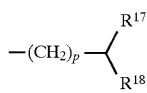

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;

or $R^1$ is a group of the structure

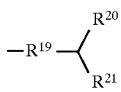

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^6$ is hydrogen or $C_1-C_4$ alkyl or $C_1-C_4$ alkenyl; all optionally substituted with 1, 2, 3 or 4 groups which may independently be any of the substituents listed in the definition of $R^5$ set out above;

$R^7$ is alkyl, aryl or arylalkyl wherein alkyl by itself or as part of arylalkyl is optionally substituted with oxo

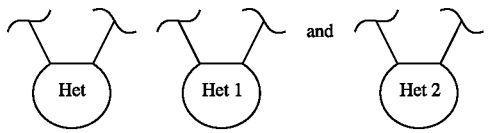

are the same or different and are independently selected from heteroaryl containing 5- or 6-ring members; and N-oxides

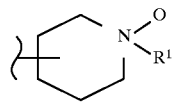

thereof; and pharmaceutically acceptable salts thereof;

with the provisos that where in the first formula X is $CH_2$, and $R^2$, $R^3$ and $R^4$ are each H, then $R^1$ will be other than 3,3-diphenylpropyl, and in the fifth formula, where one of $R^2$, $R^3$ and $R^4$ is 6-fluoro, and the others are H, $R^7$ will be other than 4-(2-methoxyphenyl).

The MTP inhibitors disclosed in U.S. application Ser. No. 548,811 filed Jan. 11, 1996, now U.S. Pat. No. 5,712,279 (file DC21h), have the structure

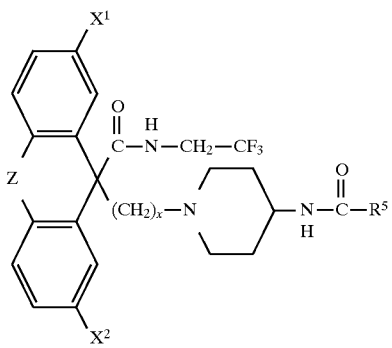

including the piperidine N-oxide thereof or a pharmaceutically acceptable salt thereof, wherein Z is a bond, O or S;

$X^1$ and $X^2$ are independently selected from H or halo;

x is an integer from 2 to 6;

$R^5$ is heteroaryl, aryl, heterocycloalkyl or cycloalkyl, each $R^5$ group being optionally substituted with 1, 2, 3 or 4 substituents which may be the same or different.

The MTP inhibitors disclosed in U.S. provisional application No. 60/017,224, filed May 9, 1996 (file HX79a*) have the structure

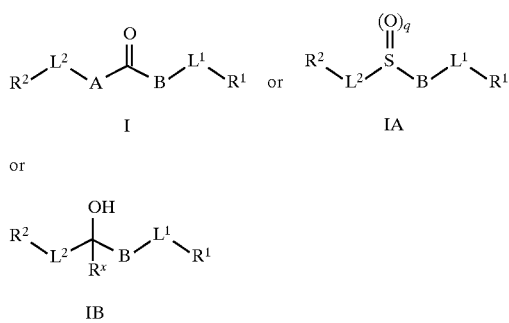

including pharmaceutically acceptable salts thereof, wherein q is 0, 1 or 2;

A is (1) a bond;

(2) —O—; or (3)

where $R^5$ is H or lower alkyl or $R^5$ together with $R^2$ forms a carbocyclic or heterocyclic ring system containing 4 to 8 members in the ring.

B is a fluorenyl-type group of the structure:

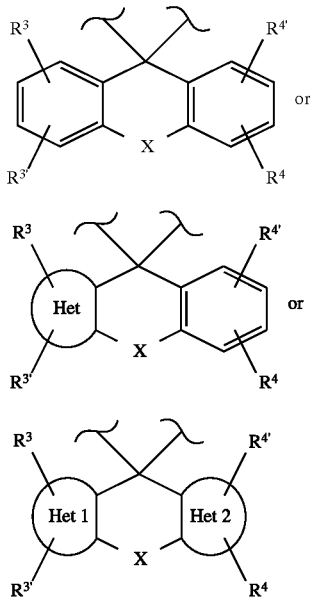

(the above B is also referred to as a fluorenyl-type ring or moiety); or

B is an indenyl-type group of the structure

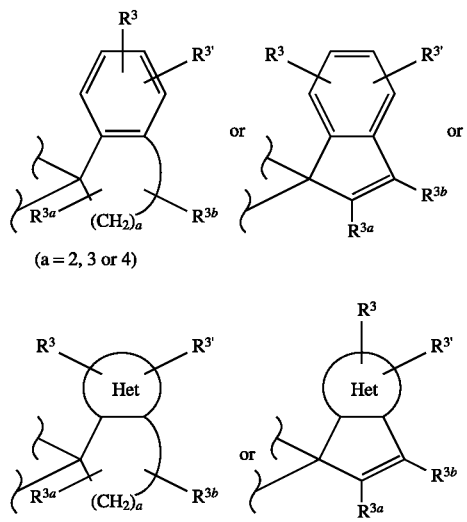

(the above B is also referred to as an indenyl-type ring or moiety);

$R^x$ is H, alkyl or aryl;

$R^1$ is alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO($R^{13}$) ($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); $R^1$ can also be aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring, such as 1,3-dioxane or 1,3-dioxolane, connected to L$^1$ (or L$^2$ in the case of R$^2$) at the 2-position); 1,3-dioxane or 1,3-dioxolane connected to L$^1$ (or L$^2$ in the case of R$^2$) at the 4-position.

The R$^1$ group may have from one to four substituents, which can be any of the R$^3$ groups or R$^1$ groups, and any of the preferred R$^1$ substituents set out below.

R$^1$ may be substituted with the following preferred substituents: alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

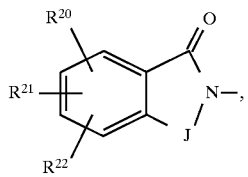

where J is: CHR$^{23}$,

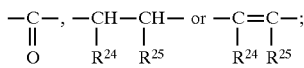

R$^{23}$, R$^{24}$ and R$^{25}$ are independently hydrogen, alkyl, alkenyl, alkynyl, aryl, arylalkyl, heteroaryl, heteroarylalkyl, cycloalkyl, or cycloalkylalkyl;

R$^{20}$, R$^{21}$, R$^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these preferred substituents may either be directly attached to R$^1$, or attached via an alkylene chain at an open position.

R$^2$ is the same or different from R$^1$ and is independently any of the groups set out for R$^1$, H, polyhaloalkyl (such as CF$_3$CH$_2$, CF$_3$CF$_2$CH$_2$ or CF$_3$) or cycloheteroalkyl, and may be substituted with one to four of any of the groups defined for R$^3$, or any of the substituents preferred for R$^1$.

L$^1$ is a linking group containing from 1 to 10 carbons in a linear chain (including alkylene, alkenylene or alkynylene), which may contain, within the linking chain any of the following: one or two alkenes, one or two alkynes, an oxygen, an amino group optionally substituted with alkyl or aryl, an oxo group; and may be substituted with one to five alkyl or halo groups (preferably F).

L$^2$ may be the same or different from L$^1$ and may independently be any of the L$^1$ groups set out above or a singe bond.

R$^3$, R$^{3'}$, R$^4$ and R$^{4'}$ may be the same or different and are independently selected from H, halogen, CF$_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

R$^{3a}$ and R$^{3b}$ are the same or different and are independently any of the R$^3$ groups except hydroxy, nitro, amino or thio;

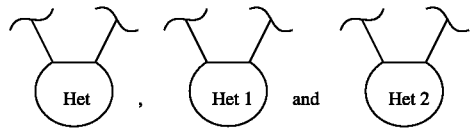

are the same or different and independently represent a 5 or 6 membered heteroaryl ring which may contain 1, 2, 3 or 4 heteroatoms in the ring which are independently N, S or O; and including N-oxides.

X (in the fluorenyl type ring) is a bond, or is one of the following groups:

 (1)

 (2)

 (3)

 (4)

 (5)

 (6)

 (7)

wherein
Y is O, N—R$^6$ or S;
n' is 0, 1 or 2;
R$^6$ is H, lower alkyl, aryl, —C(O)—R$^{11}$ or —C(O)—O—R$^{11}$;
R$^7$ and R$^8$ are the same or different and are independently H, alkyl, aryl, halogen, —O—R$^{12}$, or
R$^7$ and R$^8$ together can be oxygen to form a ketone;
R$^9$, R$^{10}$, R$^{9'}$ and R$^{10'}$ are the same or different and are independently H, lower alkyl, aryl or —O—R$^{11}$;
R$^{9''}$ and R$^{10''}$ are the same or different and are independently H, lower alkyl, aryl, halogen or —O—R$^{11}$;
R$^{11}$ is alky or aryl;
R$^{12}$ is H, alkyl or aryl.

The following provisos apply to formula I compounds:
(a) when R$^1$ is unsubstituted alkyl or unsubstituted arylalkyl, L$^1$ cannot contain amino;
(b) when R$^1$ is alkyl, L$^1$ cannot contain amino and oxo in adjacent positions (to form an amido group);
(c) when R$^2$L$^2$A— is H$_2$N—, R$^1$L$^1$ cannot contain amino;
(d) when R$^1$ is cyano, L$^1$ must have more than 2 carbons;
(e) R$^1$L$^1$ must contain at least 3 carbons.

With respect to compounds IA and IB, R$^2$L$^2$ cannot have an O or N atom directly attached to S=(O)$_q$ or CR$^x$(OH), and for IA, R$^2$L$^2$ cannot be H.

With respect to compounds IA and IB, where R$^1$ is cycloheteroalkyl, R$^1$ is exclusive of 1-piperidinyl, 1-pyrrolidinyl, 1-azetidinyl or 1-(2-oxopyrrolidinyl).

The MTP inhibitors disclosed in U.S. provisional application No. 60/017,253, filed May 10, 1996, (file HX82*) are pyrrolidine compounds and have the structure

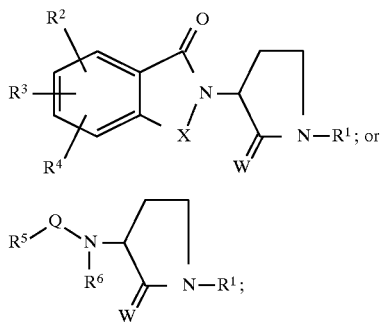   I

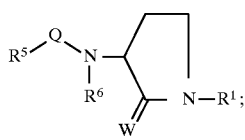   II where Q is

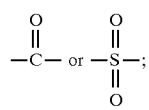

W is H,H or O;

X is CHR⁸,

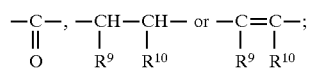

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

$R^1$ is alkyl, alkenyl, alkynyl, aryl, heteroaryl, arylalkyl (wherein alkyl preferably has at least 2 carbons, more preferably at least 3 carbons), diarylalkyl, arylalkenyl, diarylalkenyl, arylalkynyl, diarylalkynyl, diarylalkylaryl, heteroarylalkyl (wherein alkyl preferably has at least 2 carbons, more preferably at least 3 carbons), cycloalkyl, or cycloalkylalkyl (wherein alkyl preferably has at least 2 carbons, more preferably at least 3 carbons); all of the aforementioned $R^1$ groups being optionally substituted through available carbon atoms with 1, 2, 3 or 4 groups selected from halo, haloalkyl, alkyl, alkenyl, alkoxy, aryloxy, aryl, arylalkyl, alkyl-mercapto, arylmercapto, cycloalkyl, cycloalkyl-alkyl, heteroaryl, fluorenyl, heteroarylalkyl, hydroxy or oxo; or $R^1$ is a fluorenyl-type group of the structure

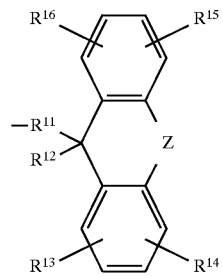   A or

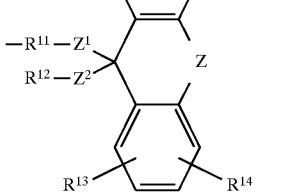   B or

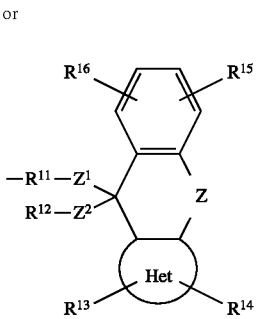   C or

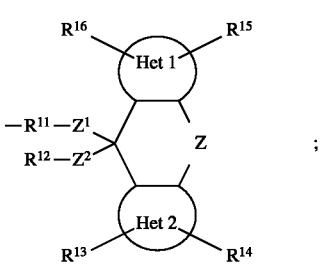   D or $R^1$ is an indenyl-type group of the structure

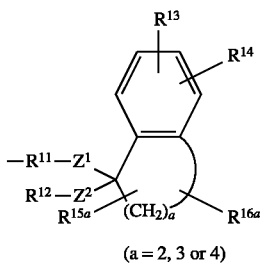   E (a = 2, 3 or 4)

or

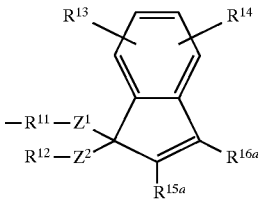   F or

-continued

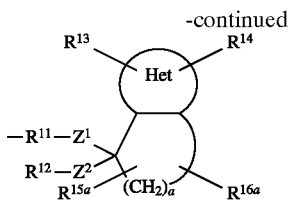

G or

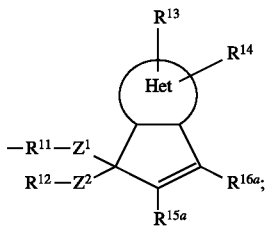

$Z^1$ and $Z^2$ are the same or different and are independently a bond, O, S,

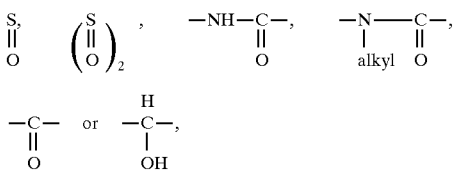

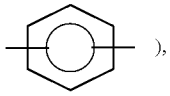

with the proviso that with respect to B, at least one of $Z^1$ and $Z^2$ will be other than a bond;

$R^{11}$ is a bond, alkylene, alkenylene or alkynylene of up to 10 carbon atoms, arylene (for example

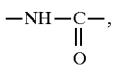), or mixed arylene-alkylene (for example

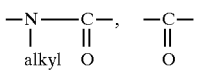)

where n is 1 to 6;

$R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cyclo-alkyl, aryloxy, alkoxy, arylalkoxy or cycloalkyl-alkyl; with the provisos that (1) when $R^{12}$ is H, aryloxy, alkoxy or arylalkoxy, then $Z^2$ is

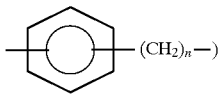

or a bond;

and (2) when $Z^2$ is a bond, $R^{12}$ cannot be heteroaryl or heteroarylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, aryl-sulfonyl, alkylthio, arylthio, aminocarbonyl, alkylcarbonyloxy, arylcarbonylamino, alkylcarbonyl-amino, arylalkyl, heteroaryl, heteroarylalkyl, or aryloxy;

$R^{15a}$ and $R^{16a}$ are independently any of the $R^{15}$ or $R^{16}$ groups except hydroxy, nitro, amino or thio;

or $R^1$ is

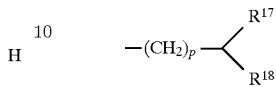

H wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

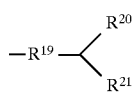

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl, alkenyl, alkynyl, aryl, alkoxy, aryloxy, arylalkoxy, heteroaryl, arylalkyl, heteroarylalkyl, cycloalkyl, cycloheteroalkyl, heteroaryloxy, cycloalkylalkyl, polycycloalkyl, polycycloalkylalkyl, cycloalkenyl, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all of the $R^5$ substituents and $R^6$ substituents (set out hereinafter) being optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, aryl or heteroaryl, or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl. Where $R^5$ is phenyl, aryl, heteroaryl or cycloalkyl; this group preferably includes an ortho hydrophobic substituent such as alkyl, haloalkyl (with up to 5 halo groups), alkoxy, haloalkoxy (with up to 5 halo groups), aryl, aryloxy or arylalkyl;

$R^6$ is hydrogen or $C_1$–$C_4$ alkyl or $C_1$–$C_4$ alkenyl;

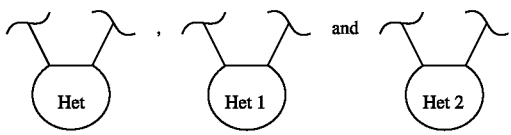

are the same or different and are independently selected from heteroaryl containing 5- or 6-ring members; and including N-oxides of the formulae I and II compounds, that is

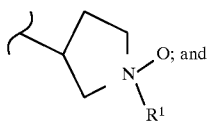

including pharmaceutically acceptable salts thereof.

The MTP inhibitors disclosed in U.S. provisional application No. 60/017,254, filed May 10, 1996, (file HX84*) are azetidine compounds which have the structure

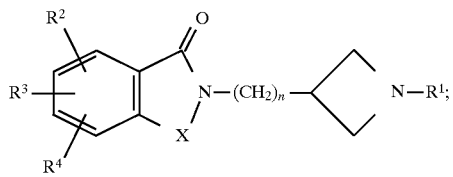

or

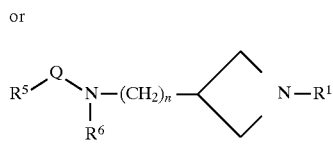

where Q is

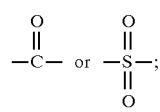

X is: $CHR^8$,

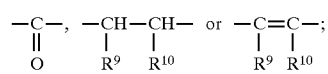

n is 0 or 1;

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

$R^1$ is alkyl, alkenyl, alkynyl, aryl, heteroaryl, arylalkyl (wherein alkyl preferably has at least 2 carbons, more preferably at least 3 carbons), diarylalkyl, arylalkenyl, diarylalkenyl, arylalkynyl, diarylalkynyl, diarylalkylaryl, heteroarylalkyl (wherein alkyl preferably has at least 2 carbons, more preferably at least 3 carbons), cycloalkyl, or cycloalkylalkyl (wherein alkyl preferably has at least 2 carbons, more preferably at least 3 carbons); all of the aforementioned $R^1$ groups being optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo; or $R^1$ is a fluorenyl-type group of the structure

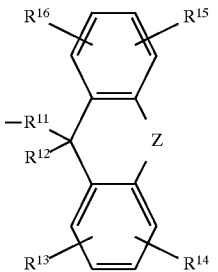 A

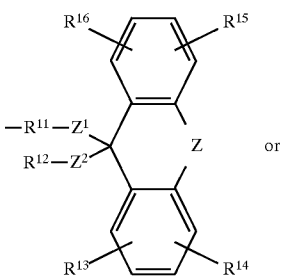 B

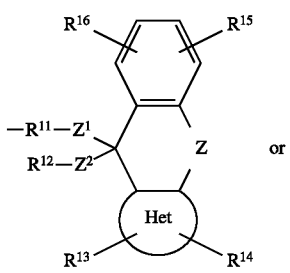 C

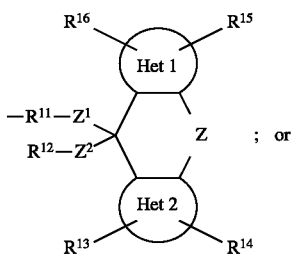 D $R^1$ is an indenyl-type group of the structure

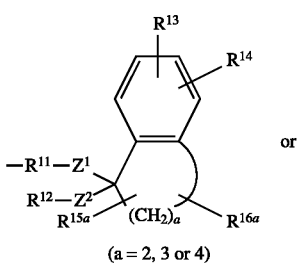 E

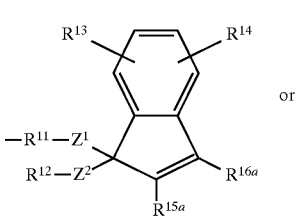 F

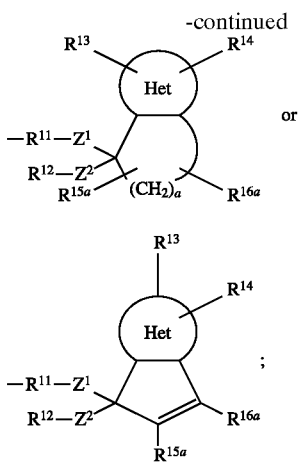

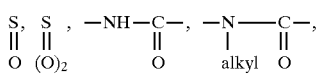

$Z^1$ and $Z^2$ are the same or different and are independently a bond, O, S,

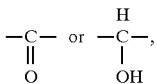

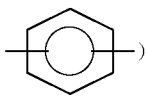

with the proviso that with respect to B, at least one of $Z^1$ and $Z^2$ will be other than a bond;

$R^{11}$ is a bond, alkylene, alkenylene or alkynylene of up to 10 carbon atoms, arylene (for example

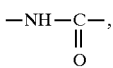

or mixed arylene-alkylene (for example

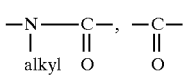

where q is 1 to 6;

$R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cyclo-alkyl, aryloxy, alkoxy, arylalkoxy or cycloalkyl-alkyl; with the provisos that (1) when $R^{12}$ is H, aryloxy, alkoxy or arylalkoxy, then $Z^2$ is

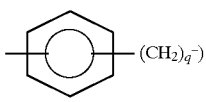

or a bond;

and (2) when $Z^2$ is a bond, $R^{12}$ cannot be heteroaryl or heteroarylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

$R^{15a}$ and $R^{16a}$ are independently any of the $R^{15}$ or $R^{16}$ groups except hydroxy, nitro, amino or thio;

or $R^1$ is

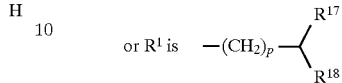

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

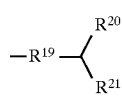

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl, alkenyl, alkynyl, aryl, alkoxy, aryloxy, arylalkoxy, heteroaryl, arylalkyl, heteroarylalkyl, cycloalkyl, cycloheteroalkyl, heteroaryloxy, cycloalkylalkyl, polycycloalkyl, polycycloalkylalkyl, cycloalkenyl, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all of the $R^5$ substituents and $R^6$ substituents (set out hereinafter) being optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, aryl or heteroaryl, or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl. Where $R^5$ is phenyl, aryl, heteroaryl or cycloalkyl; this group preferably includes an ortho hydrophobic substituent such as alkyl, haloalkyl (with up to 5 halo groups), alkoxy, haloalkoxy (with up to 5 halo groups), aryl, aryloxy or arylalkyl;

$R^6$ is hydrogen or $C_1$–$C_4$ alkyl or $C_1$–$C_4$ alkenyl;

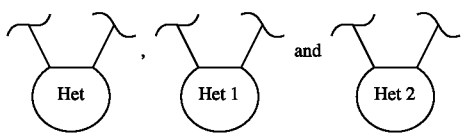

are the same or different and are independently selected from heteroaryl containing 5- or 6-ring members; and including N-oxides of the formulae I and II compounds, that is

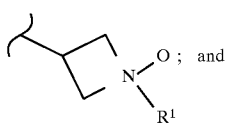

including pharmaceutically acceptable salts thereof.

Compounds disclosed as preferred in each of the above applications are preferred for use in the present invention.

Most preferred MTP inhibitors to be employed in accordance with the present invention include preferred MTP inhibitors as set out in U.S. patent application Ser. No. 548,811, filed Jan. 11, 1996, now U.S. Pat. No. 5,712,279 (file DC21h) and in U.S. provisional application No. 60/017,224, filed May 9, 1996 (file HX79a*).

Thus, preferred compounds in U.S. patent application Ser. No. 548,811, now U.S. Pat. No. 5,712,279 (file DC21h) for use herein are compounds where Z is a bond;

$X^1$ and $X^2$ are H;

$R^5$ is aryl such as phenyl substituted with (1) aryl such as phenyl,

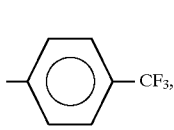 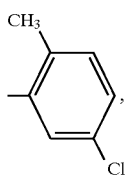

(2) heteroaryl such as

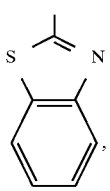 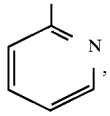

(3) halo such as Cl $R^5$ is heteroaryl such as

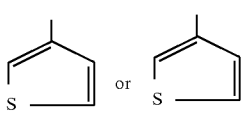

substituted with (1) aroyl such as

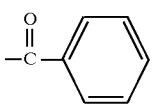

(2) arylthio such as

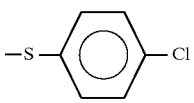

wherein the $R^5$ substituent is preferably in the position adjacent to the carbon linked to

$(CH_2)_x$ is —$(CH_2)_4$— or

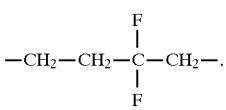

Most preferred is
9-[4-[4-[[2-(2,2,2-Trifluoroethoxy)benzoyl]amino]-1-piperidinyl]butyl]-N-(2,2,2-trifluoroethyl)-9H-fluorene-9-carboxamide

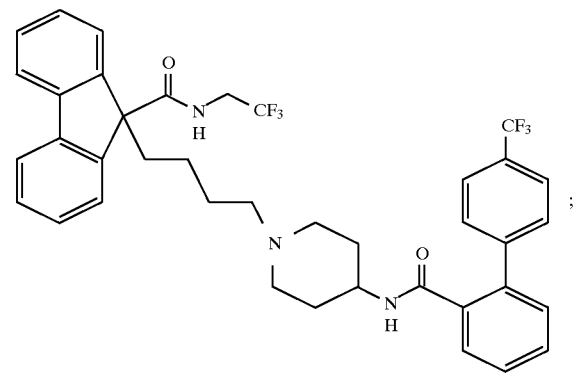

Preferred compounds in U.S. provisional application No. 60/017,224 (file HX79a*) for use herein are MTP inhibitor compounds of formula I that is

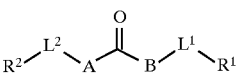

wherein A is NH,
B is

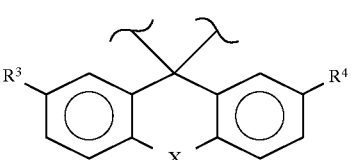

X is a bond, oxygen or sulfur; $R^3$ and $R^4$ are independently H or F.

Preferred R¹ groups are aryl, preferably phenyl, heteroaryl, preferably imidazoyl or pyridyl (preferably substituted with one of the preferred R¹ substituents: arylcarbonylamino, heteroarylcarbonylamino, cycloalkylcarbonylamino, alkoxycarbonylamino, alkylsulfonylamino, arylsulfonylamino, heteroarylsulfonylamino), PO(OAlkyl)₂, heteroarylthio, benzthiazole-2-thio, imidazole-2-thio, alkyl, or alkenyl, cycloalkyl such as cyclohexyl, or 1,3-dioxan-2-yl.

Preferred R² groups are alkyl, polyfluoroalkyl (such as 1,1,1-trifluoroethyl), alkenyl, aryl or heteroaryl (preferably substituted with one of the preferred R¹ substituents above), or PO(OAlkyl)₂.

If R² is alkyl, 1,1,1-trifluoroethyl, or alkenyl, it is preferred that R¹ is other than alkyl or alkenyl.

It is preferred that L¹ contains 1 to 5 atoms in the linear chain and L² is a bond or lower alkylene.

Preferred embodiments of formula IA and formula IB compounds of the invention include those where B, L¹, L², R¹ and R² are as set out with respect to the preferred embodiments of the formula I compounds, q is 0 or 2 and R$^x$ is H.

The other cholesterol lowering drug to be used in combination with the MTP inhibitor in accordance with the present invention is preferably an HMG CoA reductase inhibitor.

The HMG CoA reductase inhibitors suitable for use herein include, but are not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171, with pravastatin, lovastatin or simvastatin being preferred. Other HMG CoA reductase inhibitors which may be employed herein include, but are not limited to, fluvastatin, cerivastatin, atorvastatin, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-di-substituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146 A2, as well as other known HMG CoA reductase inhibitors.

In addition, phosphinic acid compounds useful in inhibiting HMG CoA reductase suitable for use herein are disclosed in GB 2205837.

The squalene synthetase inhibitors suitable for use herein include, but are not limited to, α-phosphonosulfonates disclosed in U.S. application Ser. No. 08/266,888, filed Jul. 5, 1994, now U.S. Pat. No. 5,712,396 (HX59b), those disclosed by Biller et al, J. Med. Chem. 1988, Vol. 31, No. 10, pp 1869–1871, including isoprenoid (phosphinylmethyl) phosphonates such as those of the formula

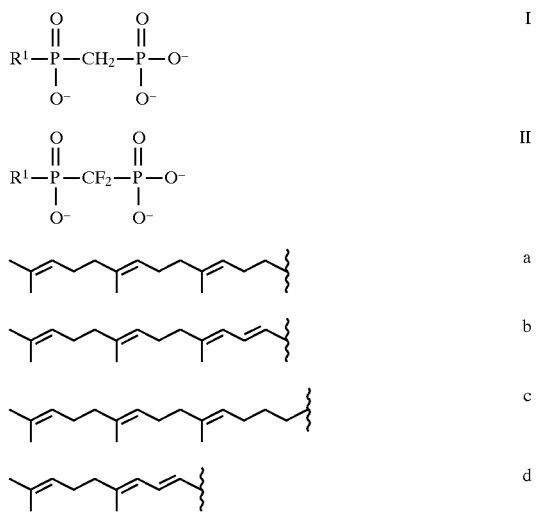

including the triacids thereof, triesters thereof and tripotassium and trisodium salts thereof as well as other squalene synthetase inhibitors disclosed in U.S. Pat. Nos. 4,871,721 and 4,924,024 and in Biller et al, J. Med. Chem., 1988, Vol. 31, No. 10, pp 1869 to 1871.

In addition, other squalene synthetase inhibitors suitable for use herein include the terpenoid pyrophosphates disclosed by P. Ortiz de Montellano et al, J. Med. Chem.; 1977, 20, 243–249, the farnesyl diphosphate analog A and presqualene pyrophosphate (PSQ-PP) analogs as disclosed by Corey and Volante, J. Am. Chem. Soc. 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U. of Utah, Abstract, Table of Contents, pp. 16, 17, 40–43, 48–51, Summary.

Preferred are pravastatin, lovastatin or simvastatin.

All of the above U.S. applications are incorporated herein by reference.

Other cholesterol lowering drugs suitable for use herein include, but are not limited to, antihyperlipoproteinemic agents such as fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Polidexide®), as well as clofibrate, lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009, and other known serum cholesterol lowering agents.

In carrying out the method of the present invention, the MTP inhibitor in combination with the cholesterol lowering drug may be administered to mammalian species, such as monkeys, dogs, cats, rats, humans, etc., and, as such, may be incorporated in a conventional systemic dosage form, such as a tablet, capsule, elixir or injectable. The above dosage forms will also include the necessary carrier material, excipient, lubricant, buffer, antibacterial, bulking agent (such as mennitol), anti-oxidants (ascorbic acid of sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result.

For oral administration, a satisfactory result may be obtained employing the MTP inhibitor in an amount within the range of from about 0.01 mg/kg to about 100 mg/kg and preferably from about 0.1 mg/kg to about 75 mg/kg.

A preferred oral dosage form, such as tablets or capsules, will contain the MTP inhibitor in an amount of from about 5 to about 500 mg, preferably from about 10 to about 400 mg, and more preferably from about 20 to about 250 mg.

For parenteral administration, the MTP inhibitor will be employed in an amount within the range of from about 0.005 mg/kg to about 10 mg/kg and preferably from about 0.005 mg/kg to about 8 mg/kg.

For oral administration, a satisfactory result my be obtained employing the HMG CoA reductase inhibitor in dosages employed, for example, for pravastatin, simvastatin, fluvastatin and lovastatin, as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain MTP inhibitor in an amount of from about 10 to about 400 mg, and the HMG CoA reductase inhibitor in an amount of from about 0.1 to about 100 mg, preferably from about 5 to about 80 mg, and more preferably from about 10 to about 50 mg.

The other serum cholesterol lowering drugs when present will be employed in dosages normally employed as indicated in the Physician's Desk Reference, for each of such agents such as in an amount within the range of from about 2 mg to about 7500 mg and preferably from about 2 mg to about 4000 mg.

The MTP inhibitor and other cholesterol lowering agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

Tablets of various sizes can be prepared, e.g., of about 2 to 2000 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of MTP inhibitor and other cholesterol lowering drug are more convenient and are preferred, especially in tablet or capsule form for oral administration.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Some of the active substances described above form commonly known, pharmaceutically acceptable salts such as alkali metal and other common basic salts or acid addition salts, etc. References to the base substances are therefore intended to include those common salts known to be substantially equivalent to the parent compound.

The formulations as described above will be administered for a prolonged period, that is, for as long as the potential for elevated cholesterol and/or triglycerides and/or atherosclerosis and other diseases set out above remains or the symptoms continue. Sustained release forms of such formulations which may provide such amounts biweekly, weekly, monthly and the like may also be employed. A dosing period of at least one to two weeks are required to achieve minimal benefit.

The following Examples represent preferred embodiments of the present invention.

EXAMPLES 1 and 2

Formulations suitable for oral administration for reducing serum cholesterol are prepared as described below.

Capsules each containing about 5 mg MTP inhibitor BMS 201,038 (Example 1) and capsules each containing about 50 mg BMS 201,038 (Example 2) are produced form the following ingredients.

| Ingredient | Example 1 Amount (mg/Capsule) | | Example 2 Amount (mg/Capsule) |
|---|---|---|---|
| BMS-201038-methane sulfonic acid salt (1) | | 5.7 | 56.9 |
| Lactose, Hydrous, NF | ca. | 151.1 | ca. 99.9 |
| Microcrystalline Cellulose, NF | | 50.0 | 50.0 |
| Pregelatinized Starch, NF | | 25.0 | 25.0 |
| Sodium Starch Glycolate, NF | | 12.5 | 12.5 |
| Colloidal Silicon Dioxide, NF | | 5.0 | 5.0 |
| Magnesium Stearate, NF | | 0.6 | 0.6 |
| Purified Water, USP or | | q.s. | q.s. |
| Water for Injection, USP | | q.s. | q.s. |
| Gray, Opaque, Size #0 Capsule Shell | | One Capsule | One Capsule |
| Total Fill Weight | | about 250.0 | about 250.0 |

(1) This amount is expressed in terms of the amount of methane sulfonic acid salt per capsule at 100% potency. This is equivalent to 5 mg and 50 mg (Examples 1 and 2, respectively) of the free base.

The MTP inhibitor BMS 201,038, and colloidal silicon dioxide are blended in a suitable blender with lactose hydrous, microcrystalline cellulose, pregelatinized starch and a portion of sodium starch glycolate. The resulting blend is wet granulated with water. The wet granulation is dried in a suitable dryer. The remaining portion of sodium starch glycolate is added to the granulation and mixed therein. Magnesium stearate is added to the granulation and mixed therein. The resulting blend is filled into capsules.

EXAMPLE 3

Pravastatin tablets (10, 20 or 40 mg as described in the 1996 PDR) and MTP inhibitor (BMS 201,238) tablets may be administered as a combination in accordance with the teachings of the present invention to lower serum cholesterol. In addition, the pravastatin and MTP inhibitor tablets may be ground up into powders and used together in a single capsule.

EXAMPLE 4

Tablets containing 500 mg clofibrate in combination with 10 mg BMS 201,038 may be employed in separate dosage forms or combined in a single capsule form to lower serum cholesterol in accordance with the present invention.

EXAMPLES 5, 6 and 7

Ciprofibrate, bezafibrate, gemfibrozil in combination with an MTP inhibitor may also be prepared in a manner described hereinbefore in Examples 1 to 3 for use in lowering serum cholesterol.

What is claimed is:

1. A pharmaceutical combination comprising an MTP inhibitor and another cholesterol lowering agent wherein the cholesterol lowering agent is selected from the group of HMG CoA reductase inhibitors or fibric acid derivatives.

2. The combination as defined in claim 1 wherein the MTP inhibitor has the structure

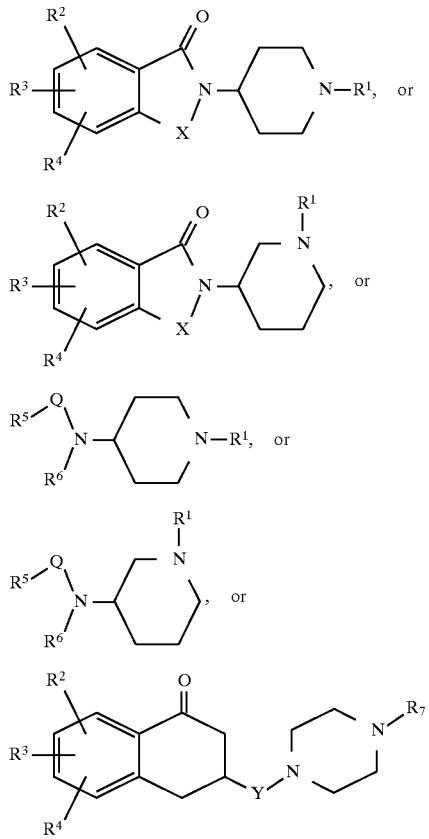

where Q is

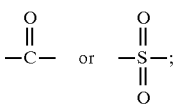

X is: $CHR^8$,

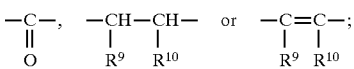

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

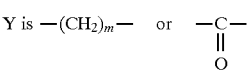

wherein m is 2 or 3;

$R^1$ is alkyl, alkenyl, alkynyl, aryl, heteroaryl, arylalkyl wherein alkyl has at least 2 carbons, diarylalkyl, arylalkenyl, diarylalkenyl, arylalkynyl, diarylalkynyl, diarylalkylaryl, heteroarylalkyl wherein alkyl has at least 2 carbons, cycloalkyl, or cycloalkylalkyl wherein alkyl has at least 2 carbons, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cyclo-alkylalkyl, heteroaryl, fluorenyl, heteroarylalkyl, hydroxy or oxo;

or R$^1$ is a fluorenyl-type group of the structure

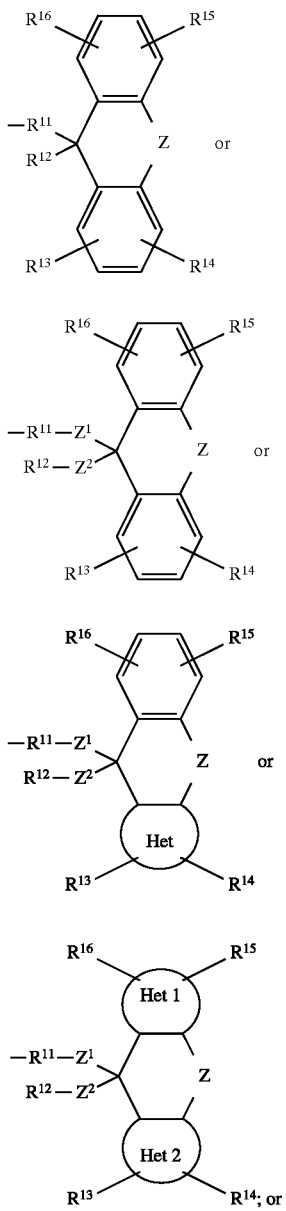

R$^1$ is an indenyl-type group of the structure

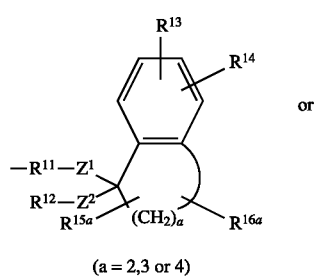
(a = 2, 3 or 4)

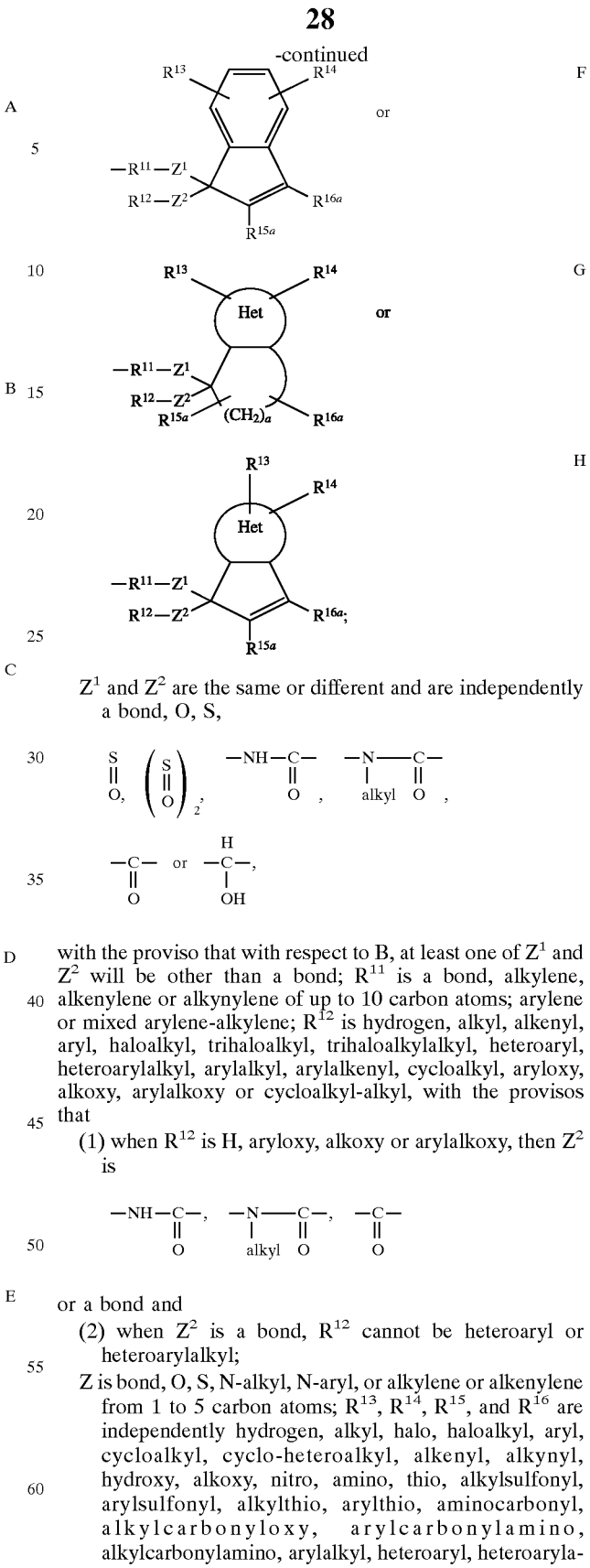

$Z^1$ and $Z^2$ are the same or different and are independently a bond, O, S, $$\underset{O}{\overset{S}{\underset{\|}{\|}}}, \quad \left(\underset{O}{\overset{S}{\underset{\|}{\|}}}\right)_2, \quad -NH-\underset{O}{\overset{C}{\underset{\|}{\|}}}-, \quad -\underset{alkyl}{\overset{N}{\underset{|}{\text{—}}}}\underset{O}{\overset{C}{\underset{\|}{\text{—}}}}-,$$

$$-\underset{O}{\overset{C}{\underset{\|}{\|}}}- \quad \text{or} \quad -\underset{OH}{\overset{H}{\underset{|}{\text{C}}}}-,$$

with the proviso that with respect to B, at least one of $Z^1$ and $Z^2$ will be other than a bond; $R^{11}$ is a bond, alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cycloalkyl, aryloxy, alkoxy, arylalkoxy or cycloalkyl-alkyl, with the provisos that
  (1) when $R^{12}$ is H, aryloxy, alkoxy or arylalkoxy, then $Z^2$ is $$-NH-\underset{O}{\overset{C}{\underset{\|}{\|}}}-, \quad -\underset{alkyl}{\overset{N}{\underset{|}{\text{—}}}}\underset{O}{\overset{C}{\underset{\|}{\text{—}}}}-, \quad -\underset{O}{\overset{C}{\underset{\|}{\|}}}-$$

or a bond and
  (2) when $Z^2$ is a bond, $R^{12}$ cannot be heteroaryl or heteroarylalkyl;
Z is bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cyclo-heteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

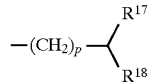

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;

or $R^1$ is a group of the structure

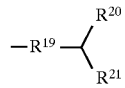

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^6$ is hydrogen or $C_1$–$C_4$ alkyl or $C_1$–$C_4$ alkenyl; all optionally substituted with 1, 2, 3 or 4 groups which may independently be any of the substituents listed in the definition of $R^5$ set out above;

$R^7$ is alkyl, aryl or arylalkyl wherein alkyl by itself or as part of arylalkyl is optionally substituted with oxo

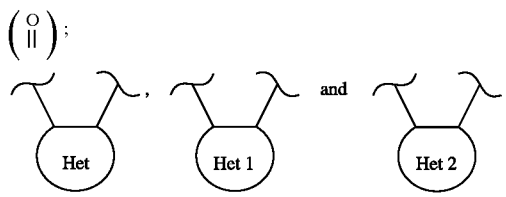

are the same or different and are independently selected from heteroaryl containing 5- or 6-ring members; and N-oxides

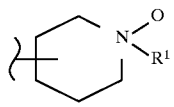

thereof; and pharmaceutically acceptable salts thereof;

with the provisos that where in the first formula X is $CH_2$, and $R^2$, $R^3$ and $R^4$ are each H, then $R^1$ will be other than 3,3-diphenylpropyl, and in the fifth formula, where one of $R^2$, $R^3$ and $R^4$ is 6-fluoro, and the others are H, $R^7$ will be other than 4-(2-methoxyphenyl).

3. The combination as defined in claim 2 wherein the MTP inhibitor has the formula

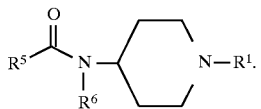

4. The combination as defined in claim 2 where in the MTP inhibitor $R^1$ is

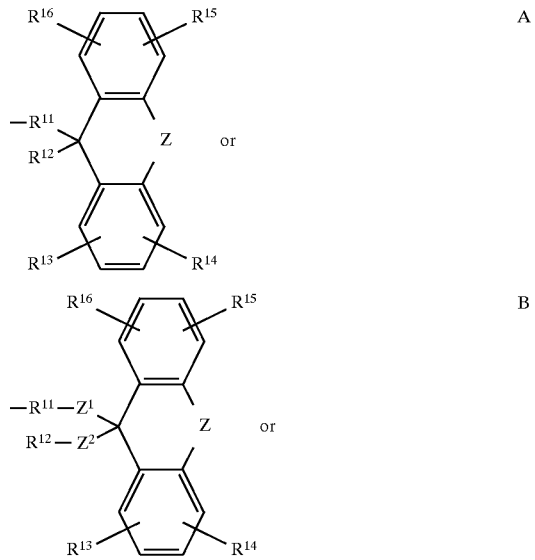

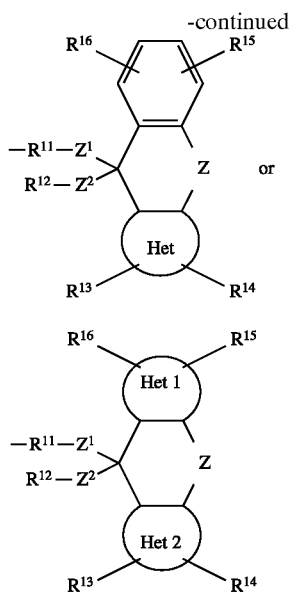

5. The combination as defined in claim 1 wherein the MTP inhibitor has the structure

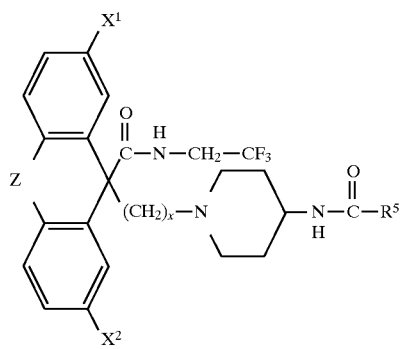

or the piperidine N-oxide thereof or a pharmaceutically acceptable salt thereof, wherein Z is a bond, O or S;

$X^1$ and $X^2$ are independently selected from H or halo;

x is an integer from 2 to 6;

$R^5$ is heteroaryl, aryl, heterocycloalkyl or cycloalkyl, each $R^5$ group being optionally substituted with 1, 2, 3 or 4 substituents which may be the same or different.

6. The combination as defined in claim 2 where in the MTP inhibitor $R^5$ is substituted with 1, 2, 3 or 4 of one or more of the following I, Cl, F, $CF_3$

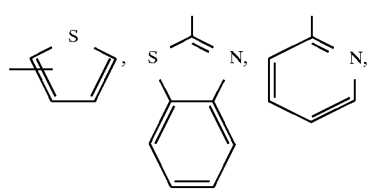

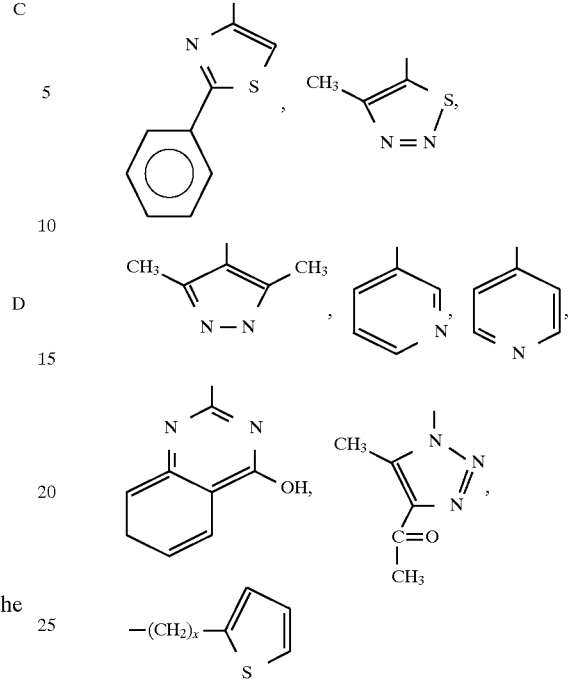

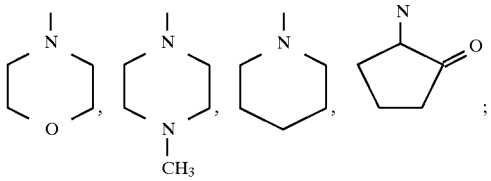

where x is 1 to 5

alkyl, phenyl, phenyl substituted with halo, alkyl, $CF_3O$, alkoxy,

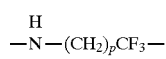

$CF_3$, or phenyl;

—N(H)—$(CH_2)_p CF_3$— where p is 1 to 5, —$N(CH_3)C_6H_5$; —S—$(CH_2)_p CF_3$ where p is 1 to 5,

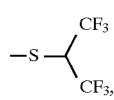

—S—alkyl,

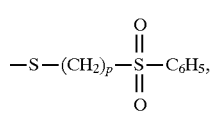

—O—(CH$_2$)$_p$—CF$_3$,

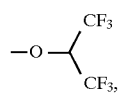

OCH$_3$; cyclohexyl,

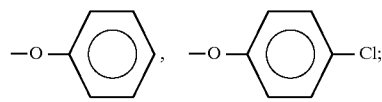

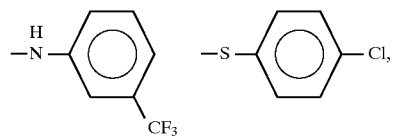

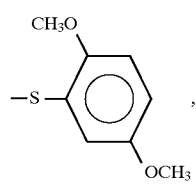

amino,

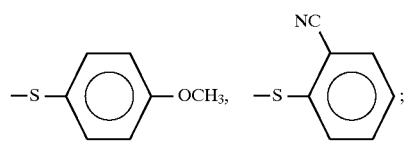

alkanoyl, alkoxycarbonyl, aroyl, heteroarylaminocarbonyl, arylalkyloxycarbonyl, —CH$_2$—S—C$_6$H$_5$,

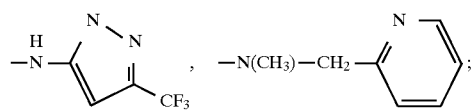

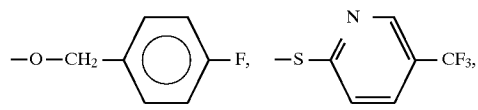

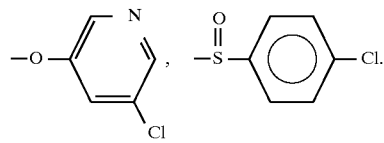

7. The combination as defined in claim 2 where in the MTP inhibitor R$^5$ is phenyl substituted with haloalkylphenyl or heteroaryl.

8. The combination as defined in claim 7 where in the MTP inhibitor R$^5$ is

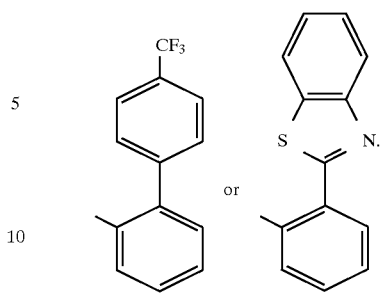

9. The combination as defined in claim 2 where in the MTP inhibitor is

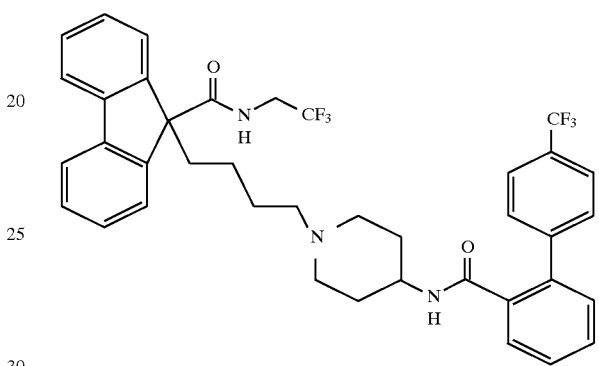

or

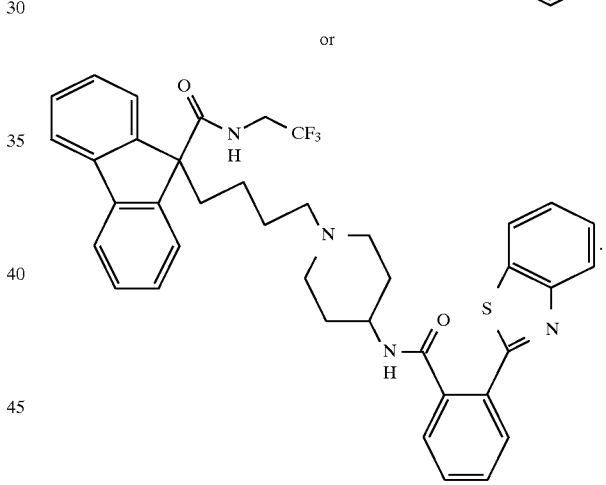

10. The combination as defined in claim 1 wherein the MTP inhibitor has the structure

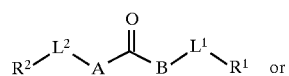   I

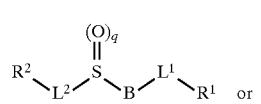   IA

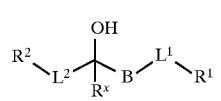   IB or pharmaceutically acceptable salts thereof, or N-oxides thereof, wherein q is 0, 1 or 2;

A is (1) a bond;
(2) —O—; or
(3)

where $R^5$ is H or lower alkyl, or $R^5$ together with $R^2$ forms a carbocyclic or heterocyclic ring system containing 4 to 8 members in the ring;

B is a fluorenyl-type group of the structure

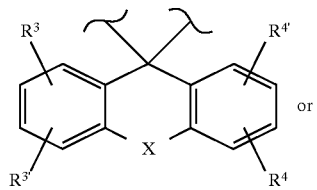 or

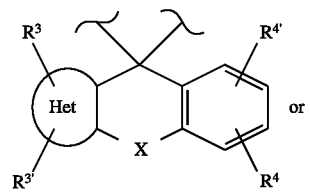 or

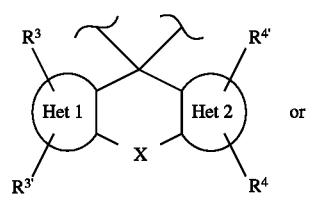 or

B is an indenyl-type group of the structure

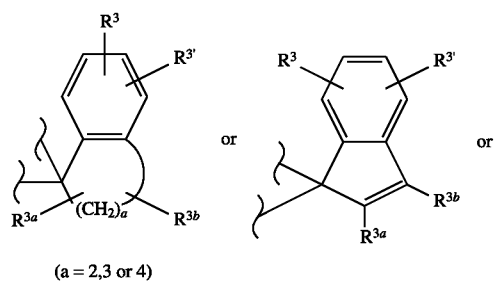

(a = 2, 3 or 4)

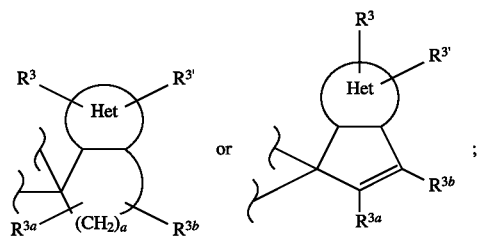 ;

$R^x$ is H, alkyl or aryl;

$R^1$ is alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO($R^{13}$) ($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring connected to $L^1$ (or $L^2$ in the case of $R^2$) at the 2-position; 1,3-dioxane or 1,3-dioxolane connected to $L^1$ (or $L^2$ in the case of $R^2$) at the 4-position; the $R^1$ group which is substituted as indicated above or may optionally be substituted with 1, 2, 3 or 4 substituents, which can be any of the $R^3$ or $R^1$ groups or alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may optionally be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

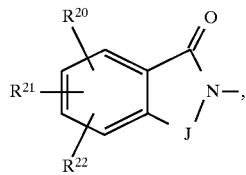

where J is: $CHR^{23}$,

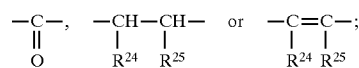

$R^{23}$, $R^{24}$ and $R^{25}$ are independently hydrogen, alkyl, alkenyl, alkynyl, aryl, arylalkyl, heteroaryl, heteroarylalkyl, cycloalkyl, or cycloalkylalkyl;

$R^{20}$, $R^{21}$, $R^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these substituents may either be directly attached to $R^1$, or attached via an alkylene at an open position;

$R^2$ is independently any of the groups set out for $R^1$, H, polyhaloalkyl, or cycloheteroalkyl, and may be optionally substituted with one to four of any of the groups defined for $R^3$ or substituents defined for $R^1$;

$L^1$ is a linking group containing from 1 to 10 carbons in a linear chain including alkylene, alkenylene or alkynylene, which may contain, within the linking chain any of the following: one or two alkenes, one or two alkynes, an oxygen, an amino group, an oxo group, acid may be substituted with one to five alkyl or halo groups;

$L^2$ may be the same or different from $L^1$ and may independently be any of the $L^1$ groups set out above or a singe bond;

$R^3$, $R^{3'}$, $R^4$ and $R^{4'}$ may be the same or different and are independently selected from H, halogen, $CF_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar-, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar which rings can be aryl, cycloalkyl, heteroaryl or cycloheteroalkyl;

$R^{3a}$ and $R^{3b}$ are the same or different and are independently any of the $R^3$ groups except hydroxy, nitro, amino or thio;

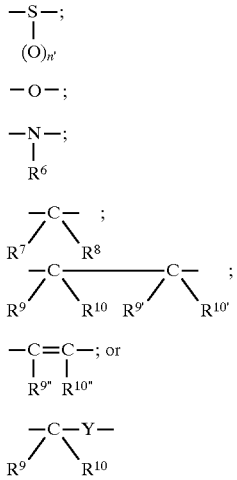

are the same or different and independently represent a 5 or 6 membered heteroaryl ring which contains 1, 2, 3 or 4 heteroatoms in the ring which are independently N, S or O; and including N-oxides;

X is a bond, or is one of the following groups:

$$-\underset{(O)_{n'}}{S}-; \quad (1)$$

$$-O-; \quad (2)$$

$$-\underset{R^6}{N}-; \quad (3)$$

$$-\underset{R^7}{\overset{R^8}{C}}-; \quad (4)$$

$$-\underset{R^9}{\overset{R^8}{C}}-\underset{R^{9'}}{\overset{R^{10'}}{C}}-; \quad (5)$$

$$-\underset{R^{9''}}{\overset{}{C}}=\underset{R^{10''}}{\overset{}{C}}-; \text{ or} \quad (6)$$

$$-\underset{R^9}{\overset{R^{10}}{C}}-Y-; \quad (7)$$

wherein

Y is O, N—$R^6$ or S;

n' is 0, 1 or 2;

$R^6$ is H, lower alkyl, aryl, —C(O)—$R^{11}$ or —C(O)—O—$R^{11}$;

$R^7$ and $R^8$ are the same or different and are independently H, alkyl, aryl, halogen, —O—$R^{12}$, or $R^7$ and $R^8$ together can be oxygen to form a ketone;

$R^9$, $R^{10}$, $R^{9'}$ and $R^{10'}$ are the same or different and are independently H, lower alkyl, aryl or —O—$R^{11}$;

$R^{9''}$ and $R^{10''}$ are the same or different and are independently H, lower alkyl, aryl, halogen or —O—$R^{11}$;

$R^{11}$ is alky or aryl;

$R^{12}$ is H, alkyl or aryl;

with the following provisos for compound of the structure

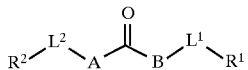

(a) when $R^1$ is unsubstituted alkyl or unsubstituted arylalkyl, $L^1$ cannot contain amino;

(b) when $R^1$ is alkyl, $L^1$ cannot contain amino and oxo in adjacent positions (to form an amido group);

(c) when $R^2L^2A$— is $H_2N$—, $R^1L^1$ cannot contain amino;

(d) when $R^1$ is cyano, $L^1$ must have more than 2 carbons;

(e) $R^1L^1$ must contain at least 3 carbons;

with respect to compounds of formulas I, IA and IB, where $R^1$ is cycloheteroalkyl, $R^1$ is exclusive of 1-piperidinyl, 1-pyrrolidinyl, 1-azetidinyl or 1-(2-oxo-pyrrolidinyl);

with respect to the sulfur containing compounds and alcohols, $R^2L^2$ cannot have an O or N atom directly attached to $S=(O)_q$ or $CR^x(OH)$, and for IA, $R^2L^2$ cannot be H.

11. The combination as defined in claim 10 wherein the MTP inhibitor has the structure

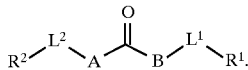

12. The combination as defined in claim 10 where in the MTP inhibitor B is a fluorenyl-type group.

13. The combination as defined in claim 10 wherein the MTP inhibitor has the formula

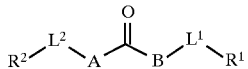

wherein B is

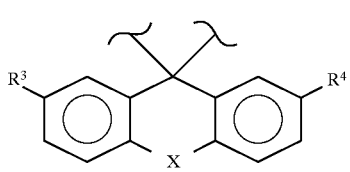

A is NH;

X is a bond, oxygen or sulfur;

$R^3$ and $R^4$ are the same or different and are H or F;

$R^1$ is aryl, phenyl, heteroaryl, imidazolyl, pyridyl, cyclohexyl, $PO(R^{13})(R^{14})$, heteroarylthio, benzthiazole-2-thio, imidazole-2-thio, alkyl, alkenyl or 1,3-dioxan-2-yl, wherein each of the above is optionally substituted;

$R^2$ is alkyl, polyfluoroalkyl, alkenyl, aryl, phenyl, heteroaryl, imidazolyl or pyridyl, wherein each of the above is optionally substituted;

$L^1$ is a chain containing 1 to 5 atoms in a linear chain;

$L^2$ is a bond or lower alkylene.

14. The combination as defined in claim 2 wherein the other cholesterol lowering drug is an inhibitor of the enzyme 3-hydroxy-3-methylglutaryl coenzyme A (HMG CoA) reductase.

15. The combination as defined in claim 2 wherein said inhibitor of the enzyme HMG CoA reductase is lovastatin, pravastatin, simvastatin, atorvastatin, fluvastatin or cerivastatin.

16. The combination as defined in claim 1 wherein the other cholesterol lowering drug is a fibric acid derivative which is gemfibrozil, fenofibrate, clofibrate, bezafibrate, ciprofibrate or clinofibrate.

17. The combination as defined in claim 1 wherein the MTP inhibitor is present in a weight ratio to said cholesterol lowering drug of within the range of from about 0.001:1 to about 1000:1.

18. The combinaiton as defined in claim 2 wherein the MTP inhibitor is BMS 201,038 and the cholesterol lowering drug is pravastatin, simvastatin, lovastatin, atorvastatin, fluvastatin or cerivastatin.

19. A method for preventing, inhibiting or treating atherosclerosis, pancreatitis or obesity in a mammalian species, which comprises administering to a patient in need thereof a therapeutically effective amount of a pharmaceutical combination as defined in claim 1.

20. A method of lowering serum lipid levels, cholesterol or triglycerides, or inhibiting or treating hyperlipemia, hyperlipidemia, hyperlipoproteinemia, hypercholesterolemia and/or hypertriglyceridemia, or preventing, inhibiting or treating atherosclerosis, pancreatitis or obesity, in a mammalian species, which comprises administering to a patient in need thereof a therapeutically effective amount of a pharmaceutical combination as defined in claim 1.

21. The method as defined in claim 20 wherein the LDL blood level is reduced to at least 20% of normal LDL blood level.

22. The method as defined in claim 20 wherein the LDL blood level is reduced to about zero.

* * * * *